US006558333B2

(12) United States Patent
Gilboa et al.

(10) Patent No.: US 6,558,333 B2
(45) Date of Patent: *May 6, 2003

(54) SYSTEM AND METHOD OF RECORDING AND DISPLAYING IN CONTEXT OF AN IMAGE A LOCATION OF AT LEAST ONE POINT-OF-INTEREST IN A BODY DURING AN INTRA-BODY MEDICAL PROCEDURE

(75) Inventors: Pinhas Gilboa, Haifa (IL); David Tolkowsky, Tel Aviv (IL); David Hollander, Raanana (IL)

(73) Assignee: Super Dimension LTD, Herzalia (IL)

( * ) Notice: Subject to any disclaimer, the term of this patent is extended or adjusted under 35 U.S.C. 154(b) by 55 days.

This patent is subject to a terminal disclaimer.

(21) Appl. No.: 09/838,238

(22) Filed: Apr. 20, 2001

(65) Prior Publication Data

US 2001/0031985 A1 Oct. 18, 2001

Related U.S. Application Data

(63) Continuation of application No. 09/179,827, filed on Oct. 28, 1998, now Pat. No. 6,226,543.

(30) Foreign Application Priority Data

Sep. 24, 1998 (IL) .............................. 1296333

(51) Int. Cl.[7] .................................. A61B 8/14
(52) U.S. Cl. ...................... 600/466; 600/410; 600/437; 600/466
(58) Field of Search ................. 600/407–471, 600/372, 310, 373–381, 481–518; 73/620–626; 367/7, 11, 130, 138; 378/98.4–98.8; 128/916, 897, 898, 899; 606/130

(56) References Cited

U.S. PATENT DOCUMENTS

| 4,697,595 A | 10/1987 | Breyer et al. |
| 5,042,486 A | 8/1991 | Pfeiler et al. |
| 5,409,000 A | 4/1995 | Imran |
| 5,443,489 A | 8/1995 | Ben Haim |
| 5,662,108 A | 9/1997 | Budd et al. |
| 6,226,543 B1 * | 5/2001 | Gilboa et al. .............. 378/98.8 |

FOREIGN PATENT DOCUMENTS

| WO | WO97/25101 | 7/1997 |
| WO | WO97/29682 | 8/1997 |
| WO | WO97/29685 | 8/1997 |
| WO | WO97/29701 | 8/1997 |
| WO | WO98/35720 | 8/1997 |
| WO | WO98/11840 | 3/1998 |

OTHER PUBLICATIONS

"*Ultrasonically marked catheter, a method for positive echographic catheter position identification*" Breyer et al, Medical and Biological Engineering and Computing May 1985 pp. 268–271.

* cited by examiner

Primary Examiner—Marvin M. Lateef
Assistant Examiner—Ali M. Imam
(74) Attorney, Agent, or Firm—Mark M. Friedman

(57) ABSTRACT

The present invention provides a method of recording and displaying in context of an image a location of at least one point-of-interest in a body during an intra-body medical procedure. The method includes establishing locations of the body, an imaging instrument and a location implement included within a catheter, and allows at least one point-of-interest to be displayed in the context of an image of the portion of the body, even in cases in which a relative location of the body and the imaging instrument are changed.

20 Claims, 3 Drawing Sheets

SYSTEM AND METHOD OF RECORDING AND DISPLAYING IN CONTEXT OF AN IMAGE A LOCATION OF AT LEAST ONE POINT-OF-INTEREST IN A BODY DURING AN INTRA-BODY MEDICAL PROCEDURE

This application is a continuation of U.S. patent application Ser. No. 09/179,827 filed Oct. 28, 1998, now issued as U.S. Pat. No. 6,226,543.

FIELD AND BACKGROUND OF THE INVENTION

The present invention relates to a system and method of recording and displaying in context of an image a location of at least one point-of-interest in a body during an intra-body medical procedure, and, more particularly, to a system and method which enable to simultaneously obtain location data of the body, of a catheter inserted into the body and of an imaging instrument used to image the catheter and the body, to thereby record and display in context of the image the location of the at least one point-of-interest in a body even when the relative location between any of the above locatable items is changed.

In many cases patients undergo procedures in which a catheter is inserted into their body (e.g., into a body cavity, such as, but not limited to, heart, lung, kidney, bladder and brain cavities). It is in many cases desirable to follow the location of the catheter within the body. This is especially the case when the catheter is a probe designed to collected local information from within the body (e.g., record electrical activity) and/or to perform a local treatment within the body (e.g., ablation). In such cases, it is important to precisely locate the catheter within the body, such that the local information collected has value and/or the treatment is appropriately locally applied. To this end, methods have been developed in which an imaging apparatus is employed to provide an image of the body, whereas a locating implement combined with location implements (e.g., transmitters or receivers of electromagnetic or acoustic waves) to which the locating implement (receiver or transmitter, respectively) is compatible, and which are attached to the body of the patient and to the tip of the catheter, are employed to determine the location in space of the catheter and preferably also the body of the patient. However, the prior art fails to teach the co-establishment of the location of the imaging apparatus or the image coordinates, such that points-of-interest in the body are recordable, displayable and most importantly projectable onto an image of the body of the patient taken from another angle during the same procedure or during another, later procedure.

The following discussion of prior art, as well as most of the embodiments discussed hereinunder, focus on cardiac applications where the applicability of catheter probes in combination of imaging has found many uses.

About 150,000 patients in the U.S. and about a similar number of patients in other parts of the globe suffer from cardiac arrhythmia and are treated in an electro-physiology (EP) laboratory each year. Most of these patients undergo a procedure in which selected portions of their heart tissue are ablated.

Cardiac arrhythmia is the result of improper progression of electrical signals for contraction across the heart tissue. The common cases of cardiac arrhythmia are accessory pathways, ventricular tachycardia, supra ventricular tachycardia, AV node reentry and atrial tachycardia.

In addition, some atrial fibrillation symptoms, including typical anti clockwise and clockwise flutter, are also treated by ablation.

Until recently, fibrilation and non-typical flutter was treated by implantation of a defibrillator (AICD), however, recent studies show that maze procedure may also be effective.

A typical EP laboratory includes the following equipment: A steerable X-ray transillumination device, typically a C-mount transluminance fluoroscope; an electrocardiogram unit for recording electric signals obtained by ECG and by electrodes inserted into the heart via catheters to record inner heart electric signals; a radio-frequency unit to effect ablation via RF electrode also engaged with one of the catheters; a pacemaking unit, also operable via one of the catheter; and a computer and display unit for recording and presenting in real-time the electric signals derived from the heart of the patient.

Each procedure involves a staff including at least two physicians and a nurse. One of the physicians inserts, advances and steers the catheters within the body of the patient, while the other operates the computer and the other equipment. The tips of one or more (typically two) reference catheters are inserted into acceptable reference locations within the heart, typically the coronary sinus (CS) and/or to the right ventricular apical (RVA). The reference catheters include electrodes which measure reference electric signals from the inner surface of the heart tissue. The RVA catheter typically also serves to measure signals of the His boundle. A steerable mapping/ablation/pacemaking catheter in also inserted into the heart and serves to collect electric signals for mapping the electrical activity within the heart, for pacemaking and, in some cases, for ablation of selected locations in the heart. These data may be used as an electrophysiology real time imaging of the heart.

During the procedure, the heart region is transilluminated via the transillumination device and the catheters described are inserted into the heart from the inferior vena cava or the superior vena cava to the right atrium and, if so required, through the tricuspid valve to the right ventricular. Operation in the left portion of the heart is performed via Fossa ovalis to the left atrium and further through the Miteral valve to the left ventricle. In most cases the problem causing cardiac arrhythmia is known and the procedure is pre-planned. Accordingly, electric signals mapping of the region of interest is effected to locate the precise point to be ablated. Following ablation, the heart is triggered by the pacemaking unit to a series of contractions to see if the ablation solved the problem. In many cases the ablation procedure is repeated a number of times until a desired result is achieved.

According to the present methodology, knowing the three dimensional location of the steerable catheter tip within the heart cavity depends on a large number of data parameters and visual memorization and is therefore highly subjective. It is clear that movements of the catheter along the transillumination lines (Z axis) are at all not detectable since the image is two dimensional. In addition, the heart tissue itself is transparent to X-rays and it is therefore hardly or not imageable. The reference catheters serve an important function in this respect. While the position of the mapping/ablation/pacemaking catheter along the X and Y axes is provided by the transillumination image, the position of that catheter along the Z axis is evaluated by the steering physician according to the electrical signals recorded therefrom as compared to those signals recorded by the reference electrodes. Thus, the three dimensional location of the mapping/ablation/pacemaking catheter is subjectively established by experience, memorization and analysis of a large number of data parameters as opposed to objective criteria. These difficulties are more critical when it is required to return accurately to a location already mapped for further treatment. It is furthermore critical, when it is required to return to a location ablated before since while the catheter is in its ablation mode, its electric signals mapping function must be turned off. As a result, completely undetectable and undesirable location shifts, especially along the Z axis are sometimes experienced.

A catheter which can be located in a patient using an ultrasound transmitter allocated to the catheter is disclosed in U.S. Pat. No. 4,697,595 and in the technical note "Ultrasonically marked catheter, a method for positive echographic catheter position identification." Breyer et al., Medical and Biological Engineering and Computing. May, 1985, pp. 268–271. Also, U.S. Pat. No. 5,042,486 discloses a catheter which can be located in a patient using non-ionizing fields and superimposing catheter location on a previously obtained radiological image of a blood vessel.

There is no discussion in either of these references as to the acquisition of a local information, particularly with electrical activation of the heart, with the locatable catheter tip and of possible superimposition of this local information acquired in this manner with other images, particularly with a heart chamber image.

U.S. Pat. No. 5,443,489 teaches an apparatus and method for the treatment of cardiac arrhythmias directed to a method for ablating a portion of an organ or bodily structure of a patient, which comprises obtaining a perspective image of the organ or structure to be mapped; advancing one or more catheters having distal tips to sites adjacent to or within the organ or structure, at least one of the catheters having ablation ability; sensing the location of each catheter's distal tip using a non-ionizing field; at the distal tip of one or more catheters, sensing local information of the organ or structure; processing the sensed information to create one or more data points; superimposing the one or more data points on the perspective image of the organ or structure; and ablating a portion of the organ or structure.

U.S. Pat. No. 5,409,000 teaches endocardial mapping and ablation system for introduction into a chamber of the heart formed by a wall and having a passage leading thereto comprising a catheter probe having a distal extremity adapted to be positioned in the chamber of the heart. The catheter probe is comprised of a plurality of flexible longitudinally extending circumferentially spaced-apart arms adapted to be disposed within the chamber of the heart. Electrodes are carried by the arms and are adapted to be moved into engagement with the wall of the heart. Markers visible ultrasonically are carried by the arms for encoding the arms so that the one arm can be distinguished from another. An ablation catheter is carried by and is slidably mounted in the catheter probe and has a distal extremity movable into the chamber of the heart while the catheter probe is disposed therein. The ablation catheter has control means whereby the distal extremity can be moved independently of movement of the catheter probe while the distal extremity of the catheter probe is in the chamber of the heart. An ablation electrode is carried by the distal extremity of the ablation catheter. Ultrasonic viewing means is carried by the distal extremity of the ablation catheter. The distal extremity of the ablation catheter is movable into positions to view ultrasonically the markers carried by the arms of the catheter probe so that the arms can be identified and the spacing of the arms can be ascertained.

Additional prior art of relevance includes WO 97/25101, WO 98/11840, WO 97/29701, WO 97/29682, WO 97/29685 and U.S. Pat. No. 5,662,108. It will be appreciated that U.S. Pat. Nos. 5,409,000 and 5,662,108, both are incorporated by reference as if fully set forth herein, teach real time electrophysiology imaging.

However, the above cited prior art, and in particular U.S. Pat. No. 5,443,489 and U.S. Pat. No. 5,409,000, which in some aspects of the present invention are considered the closest prior art, fail to teach establishment of the location of the imaging apparatus employed. This, in turn, is associated with a major limitation because it is in many cases advantageous to image the patient from different angles, so as to obtain images of different planes thereof. Yet, any catheter location data (point-of-interest) recorded in context of an image obtained from a certain relative orientation is non-projectable onto images obtained from other orientations, because the location in space of the imaging device is not monitored or established.

In addition, during ablation procedures as described hereinabove, it is in many cases advantageous to know an exact former ablation point, because if the application of ablation was either to an excessively small area, or non-precise, it is required to reablate tissue close to the ablated area. The above apparatuses and methods, while teaching the recording of heart functionality for identifying active sites therein, fail to teach the recording of other points-of-interest, such as, but not limited to, points to which ablation has been applied, therefore preventing the accurate relocation of such sites for nearby ablation as required from time to time.

Furthermore, as further detailed hereinunder, the records, obtained using the above apparatuses and methods, cannot be retrieved and used in later procedures applied to the same patient, whereas according to some of the embodiments according to the present invention such ability is realized.

The ability to record points-of interest will also find benefits in percutanious myocardial revascularization (PMR) in which holes are drilled into the heart muscle to provide for blood into the muscle. The exact spacing and positioning of the holes is crucial and can be monitored using the method and system according to the present invention in a better way as compared with the prior art. The present invention also finds uses and advantages in flexible catheter (as opposed to solid instruments) based neurosurgeries combined with imaging. In particular the present invention is advantageous when corrective procedures are applied to the same patient at a later date.

There is thus a widely recognized need for, and it would be highly advantageous to have, a method and system devoid of the above limitations. Especially, there is a widely recognized need for, and it would be highly advantageous to have, a system and method which enable to simultaneously obtain location data of the body of a patient, of a catheter inserted into the body of the patient and of an imaging instrument used to image the catheter and the body, to thereby record and display in context of an image generated by the instrument the location of at least one point-of-interest in the body even when the relative location between any of the above locatable items is changed.

SUMMARY OF THE INVENTION

According to one aspect of the present invention there is provided a method of recording and displaying in context of an image a location of at least one point-of-interest in a body during an intra-body medical procedure, the method comprising the steps of (a) establishing a location of the body; (b) inserting at least one catheter into a portion of the body, the at least one catheter including a first location implement;

(c) using an imaging instrument for imaging the portion of the body; (d) establishing a location of the imaging instrument; (e) advancing the at least one catheter to at least one point-of-interest in the portion of the body and via a locating implement recording a location of the at least one point-of-interest; and (f) displaying and highlighting the at least one point-of-interest in context of an image of the portion of the body, the image being generated by the imaging instrument; such that, in course of the procedure, the locations of the body, the at least one catheter and the imaging instrument are known, thereby the at least one point-of-interest is projectable and displayable in context of the image even in cases whereby a relative location of the body and the imaging instrument are changed.

According to another aspect of the present invention there is provided a system of recording and displaying in context of an image a location of at least one point-of-interest in a body during an intra-body medical procedure, the system comprising (a) a first mechanism for establishing a location of the body; (b) at least one catheter insertable into a portion of the body, the at least one catheter being supplemented with a first location implement; (c) an imaging instrument for imaging the portion of the body; (d) a locating implement for locating the first location implement and for establishing a location of the at least one catheter; and (e) a second mechanism for establishing a location of the imaging instrument; such that, by inserting the at least one catheter into the portion of the body; using the imaging instrument for imaging the portion of the body; establishing a location of the imaging instrument; advancing the at least one catheter to at least one point-of-interest in the portion of the body and recording a location of the at least one point-of-interest; so that in course of the procedure, the locations of the body, the at least one catheter and the imaging instrument are known, the at least one point-of-interest is projectable and displayable in a highlighted fashion in context of an image of the portion of the body generated by the imaging instrument even in cases where a relative location of the body and the imaging instrument are changed.

According to further features in preferred embodiments of the invention described below, the first mechanism includes a second location implement attachable onto the body, whereas establishing the location of the body is effected via the locating implement.

According to still further features in the described preferred embodiments the second location implement and the locating implement form a locating system selected from the group consisting of electromagnetic locating system, magnetic locating system, acoustic locating system, and stereopair optical system.

According to still further features in the described preferred embodiments the first mechanism is effected by ensuring that the body is fixed at a known location during the procedure.

According to still further features in the described preferred embodiments the first mechanism is effected by image processing of features in the image.

According to still further features in the described preferred embodiments the features are imageable markers made is contact with the body.

According to still further features in the described preferred embodiments the first mechanism is synchronized with physiological activity of the body.

According to still further features in the described preferred embodiments the at least one catheter includes a probing catheter.

According to still further features in the described preferred embodiments the at least one catheter having an ablation ability.

According to still further features in the described preferred embodiments the at least one catheter includes a sensor for sensing local information within the body.

According to still further features in the described preferred embodiments the at least one catheter includes a plurality of electrodes simultaneously collecting local electric information from inner walls of a heart cavity. In one example, the catheter includes a plurality of flexible longitudinally expanding circumferentially spaced-apart arms adapted to be disposed within a chamber of a heart. In another it includes an inflatable balloon supplemented with such electrodes.

According to still further features in the described preferred embodiments the at least one catheter includes a strain gauge.

According to still further features in the described preferred embodiments the at least one catheter includes a plurality of first location implements along at least a part of its length, each of the plurality of first location implements is locationable via the locating implement.

According to still further features in the described preferred embodiments the first location implement and the locating implement form a locating system selected from the group consisting of electromagnetic locating system, magnetic locating system and acoustic locating system.

According to still further features in the described preferred embodiments the imaging instrument is a real-time imaging instrument.

According to still further features in the described preferred embodiments the real-time imaging instrument is selected from the group consisting of ultrasound, fluoroscope and electrophysiology imaging.

According to still further features in the described preferred embodiments the imaging instrument is a non-real-time imaging instrument.

According to still further features in the described preferred embodiments the imaging instrument provides a primary image of the portion of the body.

According to still further features in the described preferred embodiments the imaging instrument provides a secondary image of the portion of the body.

According to still further features in the described preferred embodiments the imaging instrument is an electro physiological imaging system.

According to still further features in the described preferred embodiments the imaging instrument is designed to provide an image which corresponds to a vitality map of a tissue.

According to still further features in the described preferred embodiments the imaging instrument is adapted for simultaneously generating at least two images each of a different plane.

According to still further features in the described preferred embodiments the non-real-time imaging instrument is selected from the group consisting of computer aided tomography (CT), magnetic resonance imaging (MRI), proton emission tomography (PET) and three dimensional ultrasound.

According to still further features in the described preferred embodiments the second mechanism is effected by attaching a second location implement onto the imaging instrument and establishing the location of the imaging instrument via the locating implement.

According to still further features in the described preferred embodiments the second location implement and the locating implement form a locating system selected from the group consisting of electromagnetic locating system, magnetic locating system, acoustic locating system, and stereopair optical system.

According to still further features in the described preferred embodiments the second mechanism is effected by image processing of features in the image and by location information regarding the features.

According to still further features in the described preferred embodiments the features are imageable markers made is contact with the body.

According to still further features in the described preferred embodiments the features are imageable markers on the at least one catheter.

According to still further features in the described preferred embodiments the second mechanism is effected by a positioning implement inherent to the imaging instrument.

According to still further features in the described preferred embodiments the at least one point-of-interest is within a heart in the body.

According to still further features in the described preferred embodiments the at least one catheter has treatment ability, whereas the at least one point-of-interest is at least one point treated by the at least one catheter.

According to still further features in the described preferred embodiments the treatment is ablation or percutanious myocardial revascularization (PMR).

According to still further features in the described preferred embodiments the at least one point-of-interest is at least one point located at a displacement relative to the at least one point treated by the at least one catheter.

According to still further features in the described preferred embodiments the at least one catheter includes a sensor for sensing local information within the body, whereas the at least one point-of-interest is established in accordance with the local information.

According to still further features in the described preferred embodiments the portion of the body is a cavity within the body.

According to still further features in the described preferred embodiments the portion of the body is selected from the group consisting of heart, lung, kidney, bladder, brain, colon and blood vessels.

According to still further features in the described preferred embodiments at least one of the locations is determined in at least three degrees of freedom.

According to still further features in the described preferred embodiments at least one of the locations is determined in at least four degrees of freedom.

According to still further features in the described preferred embodiments at least one of the locations is determined in at least five degrees of freedom.

According to still further features in the described preferred embodiments at least one of the locations is determined in at least six degrees of freedom.

According to still further features in the described preferred embodiments the at least one point-of-interest is highlighted in a distinctive fashion indicative of its nature or properties.

According to still further features in the described preferred embodiments the at least one point-of-interest includes a plurality of points-of-interest all having a common nature or property and are highlighted by a line connecting thereamongst.

According to still further features in the described preferred embodiments the system further comprising (f) at least one additional imaging instrument for imaging the portion of the body; and (g) a third mechanism for establishing a location of the at least one additional imaging instrument, so as to enable displaying and highlighting the at least one point-of-interest in context of at least one additional image of the portion of the body, the at least one additional image being generated by the at least one additional imaging instrument; such that, in course of the procedure, the locations of the body, the at least one catheter and the at least one additional imaging instrument are known, thereby the at least one point-of-interest is projectable and displayable in context of the at least one additional image even in cases whereby a relative location of the body and the at least one additional imaging instrument is changed.

According to still further features in the described preferred embodiments displaying and highlighting the at least one point-of-interest is effected in a context of at least two images of the portion of the body, the at least two images being generated by the imaging instrument, each is of a different plane of the portion of the body.

According to still further features in the described preferred embodiments the at least two images are displayed simultaneously.

According to still further features in the described preferred embodiments the at least two images are of at least two orthogonal planes.

According to still further features in the described preferred embodiments the system further comprising a memory module for receiving and storing in memory the image data and/or the at least one point-of-interest data.

According to still further features in the described preferred embodiments the locating implement is connected to the imaging instrument.

The present invention successfully addresses the shortcomings of the presently known configurations by providing a system and method which enable the co-locating of a body of a patient, of a catheter inserted into a portion therein and of an imaging instrument imaging that portion, such that points-of-interest are projectable among images of different planes or sources.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
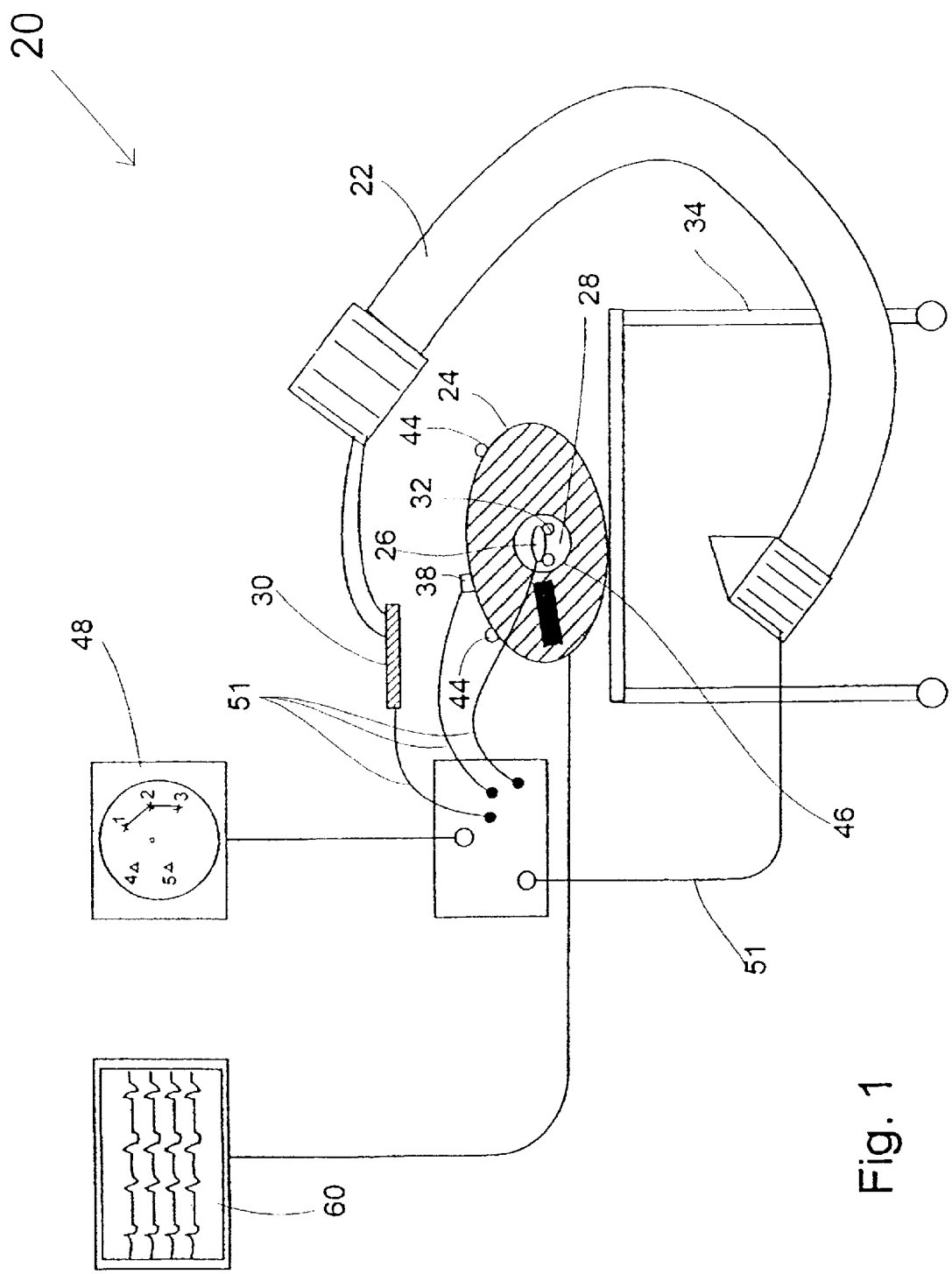
FIG. 1 is a schematic cross-sectional depiction of a preferred embodiment of a system according to the present invention.

The present invention is of a system and method which enable to simultaneously obtain location data of the body, of a catheter inserted into the body and of an imaging instrument used to image the catheter and the body which can be used to simultaneously obtain location data of the body, of a catheter inserted into the body and of an imaging instrument used to image the catheter and the body. Specifically, the present invention can be used to record and display in context of the image the location of the at least one point-of-interest in a body even when the relative location between any of the above locatable items is changed.

The principles and operation of a system and method according to the present, invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
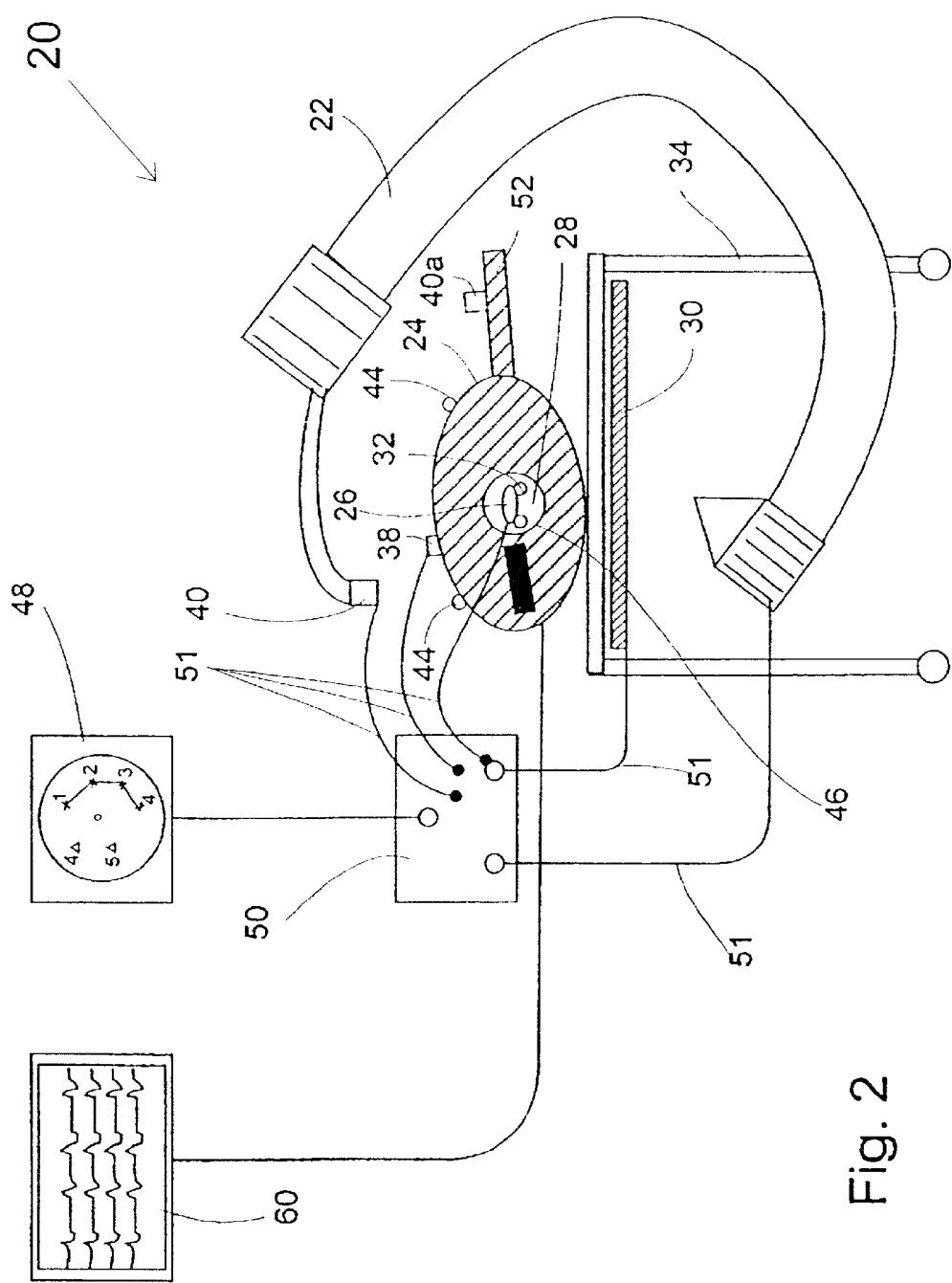
FIG. 2 is a schematic cross-sectional depiction of another preferred embodiment of a system according to the present invention.

Referring now to the drawings, FIGS. 1 and 2 illustrate the present invention in a non-limiting fashion. Thus, according to the present invention there is provided a system for recording and displaying in context of an image a location of at least one point-of-interest in a body during an intra-body medical procedure, which system is referred to herein as system 20. System 20 includes an imaging instrument 22 for imaging a portion of a body of a patient, indicated by 24. System 20 further includes a catheter 26 insertable into in body 24, e.g., into a cavity 28 present in body 24.

As used herein in the specification and in the claims section below, the term "location" refers to a position of a point relative to a reference frame of coordinates, in three-dimension, in at least three degrees of freedom.

The gist of the present invention is the ability to determine the relative locations among body 24, catheter 26 and imaging instrument 22, such that (i) points-of-interest within body 24 can be presented (highlighted) in context of an image provided by instrument 22; (ii) such points-of-interest are presentable in context of images of different projections, obtained by one or more imaging instruments, at one or more time points before or after the logging of a point-of-interest, in other words, such points-of-interest are projectable among all such images and allow a physician to, for example, go back to a point-of-interest logged in or recorder earlier, in context of a plane image no longer presented; (iii) such points-of-interest are recordable in a memory and can be used in following procedures of the same patient performed, for example, in a different time or place; and (iv) in cases where the cavity itself is non-imageable, such as the heart chambers using a fluoroscope, such points of interest can be used to mark some reference cavity coordinates, which will help the user to know the whereabouts within the body cavity and will shorten the procedure.

This aim is achieved in part according to the present invention by a locating system. The locating system includes a locating implement 30 (typically a transmitter or receiver of electromagnetic or acoustic waves) and location implement or implements 32 (typically receiver(s) or transmitter (s) of electromagnetic or acoustic waves). Implement or implements 32 are engaged at one or plurality of locations along catheter 26, typically close to or at a tip thereof and provide location data in three or more (say four, preferably five, more preferably six) degrees of freedom of catheter 26 with respect to implement 30. Implement 30 can be located in a variety of locations. It can be anywhere within an effective distance with respect to implement(s) 32. As shown in FIG. 1, it can be implemented on imaging instrument 22. In this case, the location of catheter 26 can be determined in relation to instrument 22. As shown in FIG. 2, it can be implemented onto an operation platform 34 on which the patient lies during the medical procedure. U.S. Pat. No. 5,443,489 provides examples for receivers/transmitters which function as hereindescribed.

This aim is further achieved in part according to the present invention by establishing the location of body 24. As shown in FIGS. 1–2, according to an embodiment of the present invention a location implement 38 is attached to or within body 24 of the patient, such that the location of body 24 with respect to implement 30 is establishable in three or more (say four, preferably five, more preferably six) degrees of freedom. Attaching the location implement according to one embodiment is to one or more reference catheters inserted, for example, during cardiac procedures into the heart cavity of the patient and left unmoved therein, all as further detailed in the Background section above. According to the present invention, the location of body 24 can alternatively be determined by image processing of features in the body image obtained via the imaging instrument using, for example, pattern recognition, edge enhancement, edge detection, shape detection and the like techniques of image recognition or processing. These features can be imageable markers 44 (e.g., two or more, two are shown in FIGS. 1–2) attached thereto in known positions. Four or five appropriately distributed, and preferably distinguishable, markers, say small metal discs of differential radius, readily provide location information in six degrees of freedom (X, Y, Z, α, β and γ). Alternatively, the location of body 24 can be fixed at a known location during the procedure and therefore be known. In any case, establishing the location of body 24 can be synchronized with physiological activity of the body which causes the body or portions thereof to rhythmically move, such as breathing and heart beating. The marks and/or location implements employed can be relocated on the body of the patient in their exact former position by permanently or transiently marking the positions thereof on the body of the patient with, for example, durable ink or tattoo. Image processing or recognition techniques are well known in the art and require no further description herein.

This aim is further achieved in part according to the present invention by establishing the location of instrument 22. In a configuration wherein implement 30 is not in physical context with instrument 22, as for example shown in FIG. 1, its location serves as a reference and is therefore known. In a configuration wherein implement 30 is not in physical context with instrument 22, as for example shown in FIG. 2, instrument 22 can include a location implement 40, such that the location of instrument 22 with respect to implement 30 is establishable in three or more (say four, preferably five, more preferably six) degrees of freedom. Establishing the location of instrument 22 can also be effected according to the present invention by marking catheter 26 with imageable markers 46 combined with data of its own location and image processing. Establishing the location of the imaging instrument can alternatively be effected by a positioning implement inherent to the imaging instrument. For example, magnetic resonance imaging systems include such inherent positioning implement. Such implements record movements of parts of the instrument relative to a fixed reference coordinate system. As specifically shown in FIG. 2, according to the present invention an additional imaging instrument 52 can be employed along with instrument 22 to obtain additional images of body 24. The location of instrument 52 is established in a fashion similar to that of instrument 22, such that points-of-interest can be projected onto such additional images. A location implement 40a similar to implement 40 can be employed to establish the location of instrument 52. Alternatively, image processing as described above with respect to instrument 22 can be employed for establishing the location of instrument 52.

According to a preferred embodiment of the present invention locating implement 30 and any of the above location implements 32, 38 and/or 40 form a locating system selected from the group consisting of electromagnetic locating system, magnetic locating system and acoustic locating system. In the case of extra-body location implements, e.g., implements 38 and 40, a stereopair optical system is also applicable. U.S. Pat. Nos. 5,443,489 and 5,662,108; and WO 97/25101, WO 98/11840, WO 97/29701, WO 97/29682 and WO 97/29685 and IL patent applications No. 125626 filed Aug. 2, 1998, by the present inventor, all of which are incorporated by reference as if fully set forth herein, describe these options, which options are therefore not further described herein in detail. The presently preferred option is the one disclosed in IL patent applications No. 125626 because it enables to determine all of the location information required, as herein described, using a single system.

Thus, according to the present invention the relative locations of the body, catheter inserted therein and the imaging instrument are established. As a result, points-of-interest to which the catheter points can be recorded. Such points can thereafter be presented in context of an image taken from any orientation, because the orientation is known. Thus, by inserting the catheter into a portion of the body of the patient, using the imaging instrument for imaging that portion of the body; establishing a location of the imaging instrument; advancing the catheter (e.g., the tip thereof) to a point-of-interest in the portion of the body and recording a location of that point, so that in course of the procedure, the locations of the body, the catheter and the imaging instrument are known, as well as the magnification mode employed by the imaging instrument, the point-of-interest is projectable and displayable in a highlighted fashion in context of an image of the portion of the body generated by the imaging instrument even and especially in cases where a relative location of the body and the imaging instrument are changed.

According to another aspect of the present invention there is provided a method of recording and displaying in context of an image a location of at least one point-of-interest in a body during an intra-body medical procedure. The method is effected by implementing the following method steps, in which, in a first step, the location of the body is established. In a second step of the method, at least one catheter including a location implement is inserted into a portion of the body. In a third step of the method, an imaging instrument is used for imaging the portion of the body. In a fourth step the location of the imaging instrument is established. In a fifth step, the catheter is advanced to a point-of-interest in the portion of the body and via a locating implement a location of the point-of-interest is recorded. Whereas, in a sixth step, the point-of-interest is displayed and highlighted in context of an image of the portion of the body, the image is generated by the imaging instrument. As a result, in course of the procedure, the locations of the body, the catheter and the imaging instrument are known, thereby the point-of-interest is projectable and displayable in context of the image of the portion of the body even in cases whereby a relative location of the body and the imaging instrument are changed.

The mathematics which enables the projection of points-of-interest associated with a first system of coordinates to another, is well known and therefore requires no further description herein.

The catheter according to the present invention can be of any type. For example, it can be what is known in the art as probing catheter. As used herein in the specification and in the claims section below, the term "probing catheter" refers to a catheter equipped with a sensor for sensing biological activities (or geometry e.g., by intravascular or intracardiac ultrasound), such as, for example, electrophysiological activities. The catheter is preferably designed to provide a treatment within the body. One such treatment is ablation (e.g., radio frequency (RF) ablation). Another is the intra-body local application of a drug. Ablating catheters, as well as other preferred features used in context of the present invention, are described in U.S. Pat. No. 5,443,489, which is incorporated by reference as if fully set forth herein. Alternatively or additionally, the catheter includes local sensors for sensing local information within the body. One example include electrode sensors to record electric activity within the body. Such sensors, as well as other preferred features used in context of the present invention, are described in U.S. Pat. Nos. 5,662,108 and 5,409,000, both are incorporated by reference as if fully set forth herein. Thus, in accordance with the description in U.S. Pat. No. 5,409,000, the catheter according to one embodiment of the present invention includes a plurality of flexible longitudinally expanding circumferentially spaced-apart arms adapted to be disposed within a chamber of a heart, to thereby simultaneously record electric activity in a plurality of locations within the heart.

Figure 3:
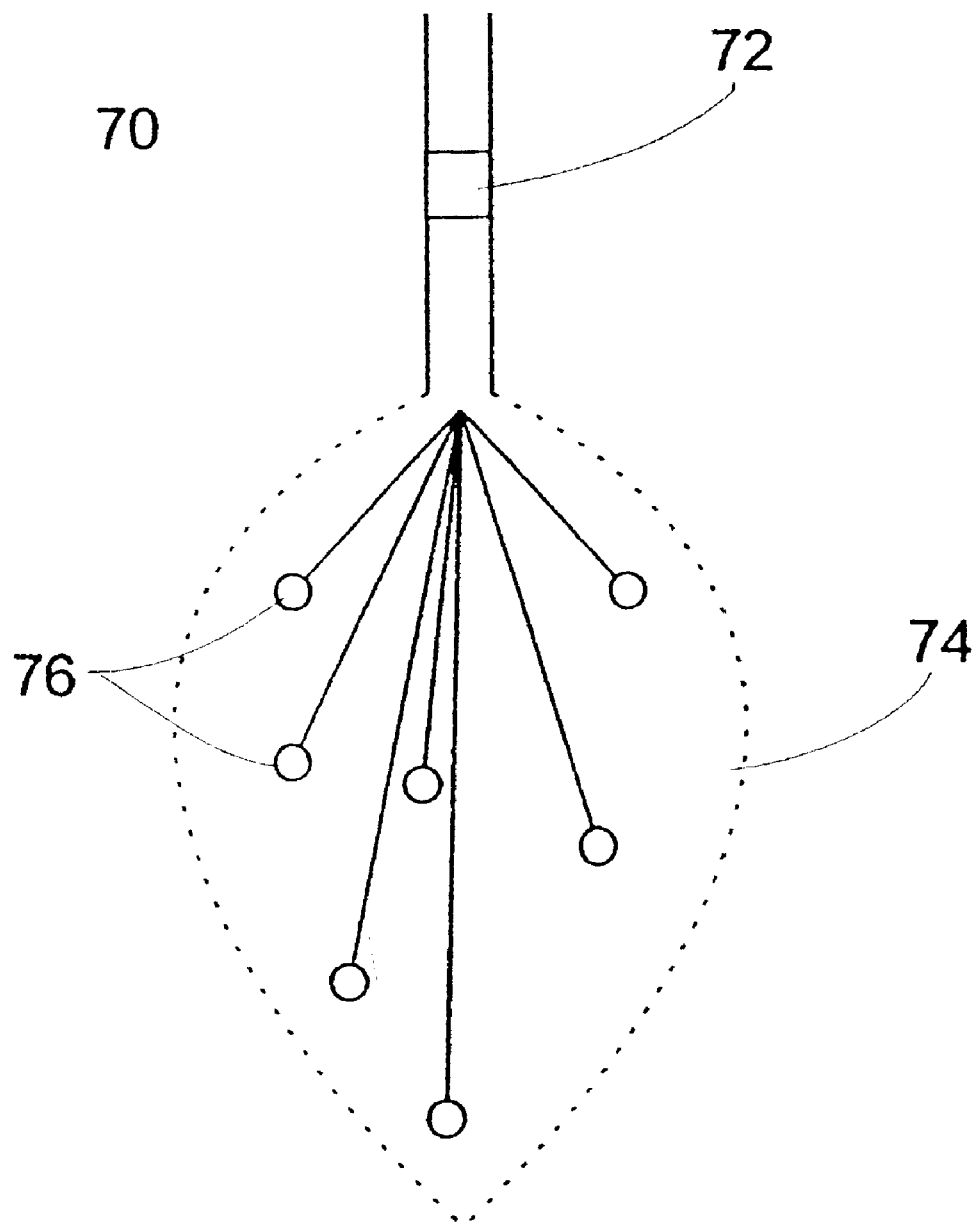
FIG. 3 is a schematic depiction of a catheter including an expandable carrier and a plurality of electrodes according to the present invention.

FIG. 3 shows a catheter 70 including a location implement 72, an expandable carrier 74 implemented at a tip of catheter 70 and a plurality of electrodes 76 carried by carrier 74.

According to a preferred embodiment of the invention, the catheter includes a strain gauge which enables to obtain location information of the tip of the catheter with relation to its body.

For cardiac applications the catheter preferably further includes a pacemaking ability (a pacemaking electrode). Catheters effective in cardiac applications according to the present invention are distributed by EP Technology, Sunnyvale, Calif., U.S.; Cordis Webster Inc., Miami, Fla., U.S.; Cardiac Pathways Corp., Sunnyvale, Calif., U.S.; and Endocardial Solutions Inc., St. Paul, Minn. U.S.

The imaging instrument according to the present invention can be of any type. For example, it can be a real-time imaging instrument, such as, but not limited to, ultrasound, fluoroscope (X-ray transillumination, e.g., a C-mount fluoroscope) and electrophysiology imaging instrument. Alternatively, the imaging instrument is a non-real-time imaging instrument, such as, but not limited to, computer aided tomography (CT), magnetic resonance imaging (MRI), proton emission tomography (PET) and three dimensional ultrasound (a software therefore is obtainable from EchoTech, Munich, Germany).

Thus, according to one embodiment of the present invention, the imaging instrument provides a primary image of a portion of the body of the treated patient.

As used herein in the specification and in the claims section below, the term "primary image" refers to a 2D image of a 3D tissue, where each picture element is achieved by an integral of some characteristic of the tissue along a line.

Whereas, according to another embodiment of the present invention, the imaging instrument provides a secondary image of said portion of the body.

As used herein in the specification and in the claims section below, the term "secondary image" refers to an image map of activity of a tissue, such as spatial physiological activity obtained by electro-physiology (EP) mapping achieved with a physiological imaging system, tissue vitality mapping, etc.

According to a preferred embodiment of the present invention the imaging instrument is adapted for simultaneously generating at least two images each of a different plane. Bi-plane fluoroscopes having two spaced apart X ray sources are well known in the art, so are multiple plane ultrasound transducers.

As used herein in the specification and in the claims section below, the term "point-of-interest" refers to any point within the body, e.g., a point on an inner side of a heart wall. The point-of-interest can reflect a point featuring local information such as specific type of electric activity. Alternatively or additionally, the point-of-interest can reflect a point to which treatment, e.g., ablation treatment, has been applied. A point-of-interest can also be displaced in known displacement magnitude and orientation from another point-of-interest. Thus, a point-of-interest can be displaced relative to a point previously treated or a point featuring specific local information previously recorded. In any case, according to a preferred embodiment of the present invention the points-of-interest are highlighted and displayed on a display 48. As shown, according to a preferred embodiment of the present invention each of the points-of-interest is highlighted in a distinctive fashion indicative of its nature or properties. Distinctively highlighting points-of-interest according to the present invention can involve application of numero-alphabet symbols, shapes, colors, etc. Some or all of the points-of-interest having a common nature or property can be highlighted by a line connecting thereamongst.

A computer 50 receives all the data, for example, via wires 51 (although wireless communication is also applicable), e.g., the image data, the data relating to the locations of the catheter, imaging instrument and the body of the patient, as well as the locations of points-of-interest which are defined by the user by pointing thereon with the catheter and activating a process for their definition as "points-of-interest", and displays the points-of-interest in context of a present or old image on display 48. Computer 50 preferably includes a memory module for receiving and storing in memory the image and/or points-of-interest data for later retrieval. The points-of-interest can be highlighted superimposed on the image in a single display 48, or alternatively, the points-of-interest and the image can be displayed separately in two different displays.

Displaying and highlighting the points-of-interest according to the present invention can be effected in context of two or more images of the portion of the body. These images are generated by one or more imaging instruments and each can represent a different plane (e.g., orthogonal planes) of the portion of the body. Such images can be displayed simultaneously or independently.

Thus, by knowing the image coordinates, the catheter coordinates and the body coordinates, points-of-interest within the body, pointed at by the catheter can be logged in and projected onto the image. Furthermore, old points-of-interest can be projected onto a present or later image, even if taken from a different orientation, therefore presenting a different plane of the body, or taken by a different imaging instrument.

The three dimensional numerical description of any one or more of the points-of-interest according to the present invention is also displayable. The co-localization of the catheter with a displayed point-of-interest can be made recognizable by a special display effect (e.g., blinking) or sound effect. Automatic steering of the catheter is also envisaged.

In cases of cardiac treatment the patient is also monitored via an electrocardiogram (ECG) system 60, as described in more detail in U.S. Pat. No. 5,443,489.

EXAMPLE

Reference is now made to the following example, which together with the above descriptions, illustrate the invention in a non limiting fashion.

Assume a first system of coordinates $\{K,L,F\}$ which defines the location of an of an imaging instrument, say a fluoroscope having a source and an imaging plane.

Assume a second system of coordinates $\{X,Y,Z\}$ which defines the location of a location implement.

Define $\{k_0,l_0,f_0\}$ as the origin of the $\{X,Y,Z\}$ system as reflected on the $\{K,L,F\}$ system of coordinates.

The $\{X,Y,Z\}$ system is rotated with respect to the $\{K,L,F\}$ system.

The rotation operator, T, is a matrix of 3×3 terms which satisfies the orthonormality condition.

The location implement implemented in the catheter is at $\{x,y,z\}$ as measured in the $\{X,Y,Z\}$ system.

The location implement is imageable and therefore will be reflected on the image plane of the imaging instrument. The location of its reflection thereon is $\{k,l,f\}$, wherein f is the distance between the radiation source and the image plane, which defines the magnification achieved while imaging.

$$\begin{bmatrix} k \\ l \\ f \end{bmatrix} = \begin{bmatrix} T_{11} & T_{12} & T_{13} \\ T_{21} & T_{22} & T_{23} \\ T_{31} & T_{32} & T_{33} \end{bmatrix} \begin{bmatrix} x \\ y \\ z \end{bmatrix} + \begin{bmatrix} k_0 \\ l_0 \\ f_0 \end{bmatrix} \quad (1)$$

If $\{k_0,l_0,f_0\}$, $\{x,y,z\}$, T and f are known, than k and l are:

$$k = f \frac{T_{11}x + T_{12}y + T_{13}z + k_0}{T_{31}x + T_{32}y + T_{33}z + f_0} \quad (2)$$

$$l = f \frac{T_{21}x + T_{22}y + T_{23}z + l_0}{T_{31}x + T_{32}y + T_{33}z + f_0} \quad (3)$$

Thus, the reflection of the tip of the catheter is calculable.

The location of the imaging instrument can be established, as further described hereinabove, via, for example, a location implement. f is, for example, measurable using an additional sensor implemented at the imaging plane.

By simple rearrangement of equations 2 and 3 above, one can obtain a set of homogenous equations:

$$f(T_{11}x+T_{12}y+T_{13}z+k_0)-k(T_{31}x+T_{32}y+T_{33}z+f_0)=0 \qquad (4)$$

$$f(T_{21}x+T_{22}y+T_{23}z+l_0)-l(T_{31}x+T_{32}y+T_{33}z+f_0)=0 \qquad (5)$$

In addition, because T is an orthonormal matrix, then:

$$T_{11}^2+T_{12}^2+T_{13}^2=1 \qquad (6)$$

$$T_{21}^2+T_{22}^2+T_{23}^2=1 \qquad (7)$$

$$T_{31}^2+T_{32}^2+T_{33}^2=1 \qquad (8)$$

$$T_{11}T_{21}+T_{12}T_{22}+T_{13}T_{23}=0 \qquad (9)$$

$$T_{11}T_{31}+T_{12}T_{32}+T_{13}T_{33}=0 \qquad (10)$$

$$T_{21}T_{31}+T_{22}T_{32}+T_{23}T_{33}=0 \qquad (11)$$

The following Table summarizes the required known parameters (middle column) for calculating unknown parameters (right column) using equations 4–11, wherein the number of measurements (n) required is indicated on the left column:

TABLE

| n | known parameters | required parameter |
|---|---|---|
| 1 | k, l, x, y, z, T, $k_0$, $l_0$ and $f_0$ | f |
| 3 | k, l, x, y, z, $k_0$, $l_0$ and $f_0$ | T |
| 4 | k, l, x, y, z and f | T, $k_0$, $l_0$ and $f_0$ |
| 5 | k, l, x, y and z | T, $k_0$, $l_0$, $f_0$ and f |

It will be appreciated by one ordinarily skilled in the art that the above mathematical description applies to any imaging instrument, including, but not limited to, ultrasound, provided that f, the magnification value thereof is either known or calculable.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of recording and displaying in context of an image a location of at least one point-of-interest in a body during an intra-body medical procedure, the method comprising the steps of:
   (a) establishing a location of the body;
   (b) inserting at least one catheter into a portion of the body, said at least one catheter including a first location implement;
   (c) using an imaging instrument for imaging said portion of the body;
   (d) establishing a location of said imaging instrument;
   (e) advancing said at least one catheter to at least one point-of-interest in said portion of the body and via a locating implement other than said imaging instrument recording a location of said at least one point-of-interest; and
   (f) displaying and highlighting said at least one point-of-interest in context of an image of said portion of the body, said image being generated by said imaging instrument;

such that, in course of said procedure, said locations of said body, said at least one catheter and said imaging instrument are known, thereby said at least one point-of-interest is projectable and displayable in context of said image even in cases whereby a relative location of said body and said imaging instrument are changed.

2. The method of claim 1, wherein establishing said location of the body is effected by attaching a second location implement onto said body and establishing the location of the body via said locating implement.

3. The method of claim 2, wherein said second location implement and said locating implement form a non-imaging locating system selected from the group consisting of electromagnetic locating system, magnetic locating system, acoustic locating system.

4. The method of claim 1, wherein establishing said location of the body is effected by ensuring that said body is fixed at a known location during the procedure.

5. The method of claim 1, wherein establishing said location of the body is effected by image processing of features in said image.

6. The method of claim 5, wherein said features are imageable markers made in contact with the body.

7. The method of claim 6, wherein said markers are distinguishable from one another.

8. The method of claim 1, wherein establishing said location of the body is synchronized with physiological activity of the body.

9. The method of claim 1, wherein said at least one catheter includes a probing catheter.

10. The method of claim 1, wherein said at least one catheter has an ablation ability.

11. A system of recording and displaying in context of an image a location of at least one point-of-interest in a body during an intra-body medical procedure, the system comprising:
   (a) a first mechanism for establishing a location of said body;
   (b) at least one catheter insertable into a portion of the body, said at least one catheter being supplemented with a first location implement;
   (c) an imaging instrument for imaging said portion of the body;
   (d) a locating implement other than said imaging instrument for locating said first location implement and for establishing a location of said at least one catheter; and
   (e) a second mechanism for establishing a location of said imaging instrument;

such that, by inserting said at least one catheter into said portion of the body; using said imaging instrument for imaging said portion of the body; establishing a location of said imaging instrument; advancing said at least one catheter to at least one point-of-interest in said portion of the body and recording a location of said at least one point-of-interest; so that in course of said procedure, said locations of said body, said at least one catheter and said imaging instrument are known, said at least one point-of-interest is projectable and displayable in a highlighted fashion in context of an image of said portion of the body generated by said imaging instrument even in cases where a relative location of said body and said imaging instrument are changed.

12. The system of claim 11, wherein said first mechanism includes a second location implement attachable onto said body, whereas establishing said location of the body is effected via said locating implement.

13. The system of claim 12, wherein said second location implement and said locating implement form a non-imaging locating system selected from the group consisting of electromagnetic locating system, magnetic locating system, acoustic locating system.

14. The system of claim 11, wherein said first mechanism is effected by ensuring that said body is fixed at a known location during the procedure.

15. The system of claim 11, wherein said first mechanism is effected by image processing of features in said image.

16. The system of claim 15, wherein said features are imageable markers made in contact with the body.

17. The method of claim 16, wherein said markers are distinguishable from one another.

18. The system of claim 11, wherein said first mechanism is synchronized with physiological activity of the body.

19. The system of claim 11, wherein said at least one catheter includes a probing catheter.

20. The system of claim 11, wherein said at least one catheter has an ablation ability.

* * * * *